(12) United States Patent
Toji et al.

(10) Patent No.: US 9,357,980 B2
(45) Date of Patent: Jun. 7, 2016

(54) ULTRASOUND DIAGNOSTIC APPARATUS AND METHOD FOR IDENTIFYING BLOOD VESSEL

(71) Applicant: KONICA MINOLTA, INC., Tokyo (JP)

(72) Inventors: Bumpei Toji, Gifu (JP); Jun Ohmiya, Kyoto (JP); Tadamasa Toma, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 215 days.

(21) Appl. No.: 14/042,797

(22) Filed: Oct. 1, 2013

(65) Prior Publication Data

US 2014/0031690 A1 Jan. 30, 2014

Related U.S. Application Data

(63) Continuation of application No. PCT/JP2012/008331, filed on Dec. 26, 2012.

(30) Foreign Application Priority Data

Jan. 10, 2012 (JP) .................................. 2012-001764

(51) Int. Cl.
*A61B 8/08* (2006.01)
*A61B 8/06* (2006.01)
(Continued)

(52) U.S. Cl.
CPC .................. *A61B 8/5223* (2013.01); *A61B 8/06* (2013.01); *A61B 8/085* (2013.01); *A61B 8/0891* (2013.01);
(Continued)

(58) Field of Classification Search
CPC .......... A61B 8/00; A61B 8/06; A61B 8/5223; A61B 8/14; A61B 8/5207; A61B 8/461; A61B 8/4245
See application file for complete search history.

(56) References Cited

U.S. PATENT DOCUMENTS 5,469,850 A 11/1995 Iizuka et al.
7,369,691 B2 5/2008 Kondo et al.
(Continued)

FOREIGN PATENT DOCUMENTS

CN 102113900 A 7/2011
CN 102188262 A 9/2011
(Continued)

OTHER PUBLICATIONS

Chinese Office Action (and English translation thereof) dated Jun. 25, 2015, issued in counterpart Chinese Application No. 201280015680.3.

(Continued)

*Primary Examiner* — Joel Lamprecht
(74) *Attorney, Agent, or Firm* — Holtz, Holtz & Volek PC

(57) ABSTRACT

An ultrasound diagnostic apparatus which detects a target blood vessel of a subject based on reflected ultrasound waves obtained, using an ultrasound probe, from the subject, the ultrasound diagnostic apparatus including: a B-mode image generation unit which generates a tomographic image of the subject, based on the reflected ultrasound waves; a blood flow image generation unit which generates blood flow information indicating a blood flow region of the subject in the tomographic image, based on the reflected ultrasound waves; and a blood flow region determination unit which determines whether or not the blood flow region corresponds to the target blood vessel, by analyzing the blood flow information generated by the blood flow image generation unit.

21 Claims, 11 Drawing Sheets

(51) Int. Cl.
*A61B 8/13* (2006.01)
*A61B 8/14* (2006.01)
*A61B 8/00* (2006.01)

(52) U.S. Cl.
CPC ... *A61B 8/13* (2013.01); *A61B 8/14* (2013.01); *A61B 8/145* (2013.01); *A61B 8/4245* (2013.01); *A61B 8/4254* (2013.01); *A61B 8/461* (2013.01); *A61B 8/466* (2013.01); *A61B 8/483* (2013.01); *A61B 8/488* (2013.01); *A61B 8/5207* (2013.01)

(56) References Cited

U.S. PATENT DOCUMENTS

| | | | |
|---|---|---|---|
| 7,738,685 | B2 | 6/2010 | Hyun et al. |
| 7,959,572 | B2 | 6/2011 | Ishihara |
| 8,542,895 | B2 | 9/2013 | Zou et al. |
| 2003/0153823 | A1* | 8/2003 | Geiser ............... G06T 7/0012 600/407 |
| 2003/0181814 | A1 | 9/2003 | Ji et al. |
| 2004/0249270 | A1 | 12/2004 | Kondo et al. |
| 2007/0167795 | A1 | 7/2007 | Hyun et al. |
| 2008/0171939 | A1 | 7/2008 | Ishihara |
| 2010/0125201 | A1 | 5/2010 | Fujii et al. |
| 2012/0130245 | A1 | 5/2012 | Chono |
| 2013/0237829 | A1 | 9/2013 | Zou et al. |
| 2014/0023251 | A1 | 1/2014 | Zou et al. |

FOREIGN PATENT DOCUMENTS

| | | |
|---|---|---|
| JP | 2000-271117 | 10/2000 |
| JP | 2004-283373 | 10/2004 |
| JP | 2004-350791 | 12/2004 |
| JP | 2004-357876 | 12/2004 |
| JP | 2006-167287 | 6/2006 |
| JP | 2007-075306 | 3/2007 |
| JP | 2007-152120 | 6/2007 |
| JP | 2007-268148 | 10/2007 |
| JP | 2008-161220 | 7/2008 |
| JP | 2008-168016 | 7/2008 |
| JP | 2009-195585 | 9/2009 |
| JP | 2011-104194 | 6/2011 |
| WO | 2011013693 A1 | 2/2011 |

OTHER PUBLICATIONS

European Office Action (in English) dated Jul. 2, 2015, issued in counterpart European Application No. 12865165.0.
International Search Report issued Jan. 29, 2013 in International (PCT) Application No. PCT/JP2012/008331.
Ainsworth CD, et al., "3D ultrasound measurement of change in carotid plaque volume: a tool for rapid evaluation of new Therapies", Stroke, Sep. 2005; 36 (9): pp. 1904-1909.
Extended European Search Report dated Oct. 22, 2015, issued in counterpart European Application No. 12865165.0.
Chinese Office Action (and English translation thereof) dated Jan. 14, 2016, issued in counterpart Chinese Application No. 201280015680.3.

* cited by examiner

ULTRASOUND DIAGNOSTIC APPARATUS AND METHOD FOR IDENTIFYING BLOOD VESSEL

CROSS REFERENCE TO RELATED APPLICATIONS

This is a continuation application of PCT International Application No. PCT/JP2012/008331 filed on Dec. 26, 2012, designating the United States of America, which is based on and claims priority of Japanese Patent Application No. 2012-001764 filed on Jan. 10, 2012. The entire disclosures of the above-identified applications, including the specifications, drawings and claims are incorporated herein by reference in their entirety.

FIELD

One or more exemplary embodiments disclosed herein relate generally to ultrasound diagnostic apparatuses and methods for identifying blood vessels, and particularly relate to an ultrasound diagnostic apparatus and a method for identifying a blood vessel, which identify a target blood vessel based on reflected ultrasound waves obtained, using an ultrasound probe, from a subject.

BACKGROUND

In recent years, ultrasound diagnostic apparatuses are being used for early discovery of arteriosclerosis, vascular diseases, and so on. Specifically, ultrasound diagnostic apparatuses are being used to measure intima-media thickness (hereinafter called IMT) which is the combined membrane thickness of the intima and media of blood vessel walls. Here, when the examiner determines the IMT or presence of plaque, the examiner manually specifies (sketches) the shape of the blood vessel adventitia and blood vessel intima in the ultrasound image, and performs the diagnosis based on this sketch. Specifically, the examiner sketches, on the B-mode image, the shape of the periphery of the adventitia as an adventitia contour line, and further sketches the shape of the periphery of the lumen as the lumen contour line. Then, at the end, the examiner performs the diagnosis for the presence of plaque, and so on, based on the shape of the sketch (see Non Patent Literature (NPL) 1.

CITATION LIST

Non Patent Literature

[Non Patent Literature 1]
Ainsworth C D, Blake C C, Tamayo A, Beletsky V, Fenster A, Spence J D, "3D ultrasound measurement of change in carotid plaque volume: a tool for rapid evaluation of new therapies.", Stroke 2005, 36 (9): 1904-1909.

SUMMARY

Technical Problem

However, an examiner needs to manually specify a blood vessel on an ultrasound image, which causes a problem that the blood vessel may not be accurately detected.

In view of this, one non-limiting and exemplary embodiment provides an ultrasound diagnostic apparatus which detects more accurately a blood vessel of interest.

Solution to Problem

In one general aspect, the techniques disclosed here feature an ultrasound diagnostic apparatus which detects a target blood vessel of a subject based on reflected ultrasound waves obtained, using an ultrasound probe, from the subject, the ultrasound diagnostic apparatus including: a tomographic image generation unit configured to generate a tomographic image of the subject, based on the reflected ultrasound waves; a blood flow information generation unit configured to generate blood flow information indicating a blood flow region of the subject in the tomographic image, based on the reflected ultrasound waves; and a blood flow region determination unit configured to determine whether or not the blood flow region corresponds to the target blood vessel, by analyzing the blood flow information generated by the blood flow information generation unit.

These general and specific aspects may be implemented using a system, a method, an integrated circuit, a computer program, or a computer-readable recording medium, such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

An ultrasound diagnostic apparatus according to one or more exemplary embodiments or features disclosed herein can identify more accurately a blood vessel of interest.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENTS (Underlying Knowledge Forming Basis of the Present Disclosure)

In relation to the ultrasound diagnostic apparatus disclosed in the Background Art section, the inventors have found the following problem.

In recent years, ultrasound diagnostic apparatuses are being used for early discovery of arteriosclerosis, vascular diseases, and so on. Specifically, ultrasound diagnostic apparatuses are being used to measure intima-media thickness (hereinafter called IMT) which is the combined membrane thickness of the intima and media of blood vessel walls. Furthermore, ultrasound diagnostic apparatuses are being used to verify the presence of plaque formed due to the narrowing of the lumen of a blood vessel. This is because it has become clear that IMT increases and plaque is formed as arteriosclerosis advances. Moreover, it is considered that arteriosclerosis advances throughout the entire body, and thus superficial carotid arteries become the main target for measurement in determining severity of the arteriosclerosis. Here, plaque refers to an elevated lesion which is a localized projection of the inner wall of the blood vessel towards the inner side (lumen) of the blood vessel. Plaque assumes various forms such as thrombus, fatty, fibrous, and so on, and can be a cause for the narrowing and occlusion of carotid arteries as well as cerebral infarction and cerebral ischemic.

Measurement of the IMT and detection of the shape of plaque using an ultrasound diagnostic apparatus is performed using ultrasound images of blood vessels. The ultrasound diagnostic apparatus sends ultrasound waves to the inside of the body of a subject from the body surface of a subject via a probe, and forms an ultrasound image (for example, a B-mode image) based on reflected waves created from the subject. Then, the examiner judges the presence of plaque by looking at the ultrasound image.

Figure 11:
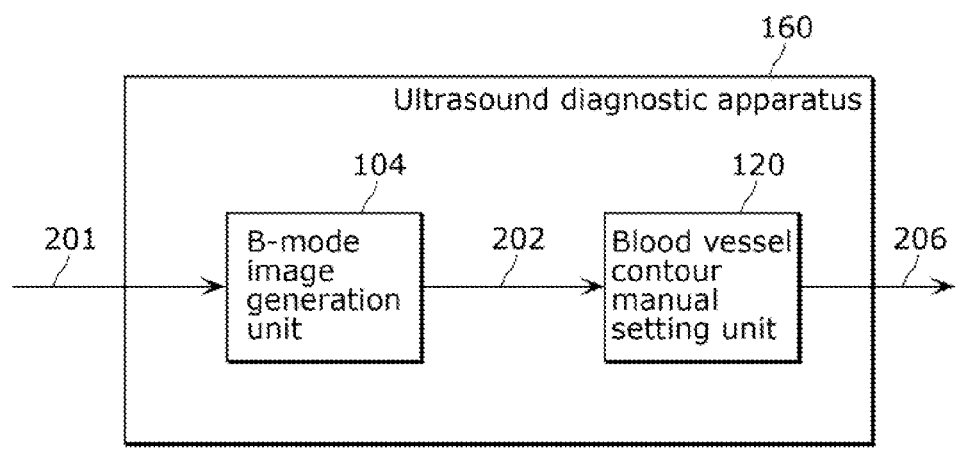
FIG. 11 is a diagram showing a first example of an assumed ultrasound diagnostic apparatus.

Here, when the examiner determines the IMT or presence of plaque, the examiner manually specifies (sketches) the shapes of the blood vessel adventitia and blood vessel intima in the ultrasound image, and performs the diagnosis based on this sketch (e.g., a configuration shown in FIG. 11). Specifically, the examiner sketches, on the B-mode image, the shape of the periphery of the adventitia as an adventitia contour line, and further sketches the shape of the periphery of the lumen as the lumen contour line. Then, at the end, the examiner performs the diagnosis for the presence of plaque, and so on, based on the shape of the sketch (e.g., see NPL 1).

However, in the method in NPL 1, after obtaining the image, the examiner needs to manually specify the positions of the adventitia contour and the intima contour of the blood vessel wall on the ultrasound image in an on-line state. Specifically, performing plaque detection using this conventional diagnostic method requires the examiner to manually specify the contours and thus is troublesome. As a result, fluctuation occurs in the results of the examination depending on examiners. Thus, there is a problem that blood vessels may not be accurately detected.

In view of this, one non-limiting and exemplary embodiment provides an ultrasound diagnostic apparatus which detects more accurately a blood vessel of interest.

In order to solve the above-described problem, an ultrasound diagnostic apparatus according to an exemplary embodiment disclosed herein is an ultrasound diagnostic apparatus which detects a target blood vessel of a subject based on reflected ultrasound waves obtained, using an ultrasound probe, from the subject, the ultrasound diagnostic apparatus including: a tomographic image generation unit configured to generate a tomographic image of the subject, based on the reflected ultrasound waves; a blood flow information generation unit configured to generate blood flow information indicating a blood flow region of the subject in the tomographic image, based on the reflected ultrasound waves; and a blood flow region determination unit configured to determine whether or not the blood flow region corresponds to the target blood vessel, by analyzing the blood flow information generated by the blood flow information generation unit.

With this, the ultrasound diagnostic apparatus can determine a blood flow region which corresponds to the target blood vessel in an ultrasound image, based on blood flow information regarding the blood flow region. The ultrasound image may include a plurality of blood flow regions including a blood flow region corresponding to the target blood vessel. In such a case, the blood flow region corresponding to the target blood vessel can be identified from among the blood flow regions, based on the blood flow information. Thus, the ultrasound diagnostic apparatus can detect more accurately the blood vessel of interest.

For example, the blood flow region determination unit is configured to perform the determination by analyzing, as the blood flow information, a position of the blood flow region in the tomographic image.

With this, the ultrasound diagnostic apparatus can identify a blood flow region based on the position of the blood flow region in the ultrasound image. An examiner sequentially obtains ultrasound images by moving (scanning) the ultrasound probe. Thus, with analysis of a position of the blood flow region in the ultrasound image, it is possible to detect the blood flow regions corresponding to an identical blood vessel in a plurality of ultrasound images. Thus, it is possible to detect more accurately the blood vessel of interest.

For example, when a plurality of the blood flow regions are arranged corresponding to respective positions on the subject at which the tomographic image including the blood flow region has been obtained, the blood flow region determination unit is configured to (i) collectively extract, as a group of blood flow regions, from among the arranged blood flow regions, blood flow regions that are separated from one another by a distance no greater than a threshold value, and (ii) perform the determination on a blood flow region included in the extracted group of blood flow regions, based on an attribute of the extracted group of blood flow regions.

With this, the ultrasound diagnostic apparatus can extract, as the blood flow regions (a group of blood flow regions) corresponding to an identical blood vessel, blood flow regions that are separated from one another in the ultrasound images by a distance no greater than a threshold value. The examiner sequentially obtains ultrasound images by moving the ultrasound probe. Thus, in the ultrasound images obtained at times that are relatively close, the blood flow regions corresponding to an identical blood vessel are present at relatively close positions. Identifying a blood flow region based on the position of the blood flow region in the ultrasound image makes it possible to detect more accurately the blood vessel of interest.

For example, when an attribute of the extracted group of blood flow regions matches an attribute of the target blood vessel which is predetermined, the blood flow region determination unit is configured to perform the determination that a blood flow region included in the extracted group of blood flow regions corresponds to the target blood vessel.

With this, when the attribute of the group of blood flow regions corresponding to an identical blood vessel matches an attribute of the target blood vessel which is predetermined, the ultrasound diagnostic apparatus can identify, as a blood flow region corresponding to the target blood vessel, the group of blood flow regions.

For example, the blood flow region determination unit is configured to perform the determination using, as an attribute of the group of blood flow regions, at least one of (i) a total number of blood flow regions included in the extracted group of blood flow regions, (ii) an area of a blood flow region having a largest area, among the blood flow regions included in the extracted group of blood flow regions, and (iii) a position of a blood flow region in each of tomographic images which are obtained at a beginning and at an end of a range on the subject in which a plurality of tomographic images including the extracted group of blood flow regions are obtained.

With this, use of these attributes makes it possible to identify more accurately a blood vessel having a Y-shape. The blood flow region having a largest area among the blood flow regions included in the group of blood flow regions corresponds to the bifurcation of the V-shape, and the beginning and the end of the Y-shape respectively correspond to the ultrasound image obtained at the start and the end of a scan using the ultrasound probe. More specifically, the ultrasound diagnostic apparatus can identify more accurately the blood vessel having the Y-shape by identifying the bifurcation and ends of the Y-shape.

For example, when a total number of the blood flow regions included in the group of blood flow regions is no greater than a predetermined number, the blood flow region determination unit is configured to perform the determination on a blood flow region included in a group of blood flow regions other than the group of blood flow regions which includes blood flow regions the total number of which is no greater than the predetermined number.

With this, the ultrasound diagnostic apparatus can identify, as a blood flow noise, a group of blood flow regions which includes a small number of blood flow regions, and exclude, from the blood flow regions on which the determination is performed, the group of blood flow regions that has been identified as the blood flow noise. Thus, the target blood vessel can be accurately detected even when blood flow information, such as the blood flow noise, other than blood flow information on the target blood vessel is present.

For example, the blood flow region determination unit is configured to determine that a blood flow region included in a group of blood flow regions, among a plurality of the groups of blood flow regions, which includes a blood flow region having a largest area corresponds to the target blood vessel.

With this, the particular blood vessel having a portion corresponding to the bifurcation of the Y-shape can be identified as the target blood vessel.

For example, in the case where a plurality of the extracted groups of blood flow regions are arranged corresponding to respective positions on the subject at which a tomographic image including each of the extracted groups of blood flow regions has been obtained, when a distance between (i) an edge of a drawing formed by an interpolation of a first group of blood flow regions and (ii) a portion of a drawing formed by an interpolation of a second group of blood flow regions is no greater than a predetermined value, the blood flow region determination unit is further configured to (i) newly and collectively extract, as a group of blood flow regions, the first group of blood flow regions and the second group of blood flow regions and (ii) perform the determination on the newly and collectively extracted group of blood flow regions.

For example, in the case where a plurality of the extracted groups of blood flow regions are arranged corresponding to respective positions on the subject at which the tomographic image including each of the extracted groups of blood flow regions has been obtained, (i) when a difference between a first position and a second position is no greater than a predetermined value, the first position being in the tomographic image of a first blood flow region included in a tomographic image obtained at a beginning or at an end of a range on the subject corresponding to the extracted groups of blood flow regions, and the second position being in the tomographic image of the second blood flow region which is included in a tomographic image obtained at the beginning or at the end of the range on the subject and is different from the first blood flow region, and (ii) when a position on the subject at which the first blood flow region has been obtained and a position on the subject at which the second blood flow region has been obtained are within a predetermined distance, the blood flow region determination unit is further configured to newly and collectively extract, as a group of blood flow regions, the group of blood flow regions including the first blood flow region and the group of blood flow regions including the second blood flow region, and perform the determination on the newly and collectively extracted group of blood flow regions.

With this, the ultrasound diagnostic apparatus can collectively group, into a group of blood flow regions, a plurality of groups of blood flow regions which have been extracted as different groups of blood flow regions, and determine whether or not the group of blood flow regions is the target blood vessel.

For example, the blood flow region determination unit is configured to perform the determination by analyzing, as the blood flow information, an area of the blood flow region in the tomographic image.

With this, the ultrasound diagnostic apparatus can identify the blood flow region based on the area of the blood flow region in the ultrasound image. An examiner sequentially obtains ultrasound images by moving (scanning) the ultrasound probe. Thus, blood flow regions corresponding to an identical blood vessel can be detected in a plurality of ultrasound images, by analyzing an area of the blood flow region in the ultrasound image. Thus, it is possible to detect more accurately the blood vessel of interest.

For example, the blood flow region determination unit is configured to perform the determination by determining the presence or absence of a pulsation-like fluctuation, by analyzing a change in area of the blood flow region in each of tomographic images which are obtained.

With this, the ultrasound diagnostic apparatus can identify, as the target blood vessel, an artery having an area that changes in a pulsation-like manner.

For example, the blood flow region determination unit is configured to perform the determination by analyzing, as the blood flow information, a direction of blood flow in the blood flow region.

For example, the blood flow region determination unit is configured to perform the determination that the blood flow region corresponds to the target blood vessel, when the direction of the blood flow in the blood flow region matches a direction of blood flow in the target blood vessel which predetermined.

With this, the ultrasound diagnostic apparatus can identify the target blood vessel based on a direction of the blood flow. The direction or the orientation of the blood flow of the target blood vessel and a rough position of the target blood vessel are conventionally known. Thus, the ultrasound diagnostic apparatus can identify the target blood vessel based on the direction of the blood flow analyzed.

For example, the ultrasound diagnostic apparatus further includes: a display unit configured to display information indicating a result of the determination performed by the blood flow region determination unit; and a modification unit configured to modify the result of the determination performed by the blood flow region determination unit, based on a request from a user to modify the information indicating the result of the determination displayed on the display unit.

With this, when a determination result by the blood flow region determination unit includes an error, the ultrasound diagnostic apparatus can modify the determination result, based on the request for modification from an examiner (user). Thus, the ultrasound diagnostic apparatus can detect more accurately the target blood vessel.

For example, the ultrasound diagnostic apparatus further includes: a provisional blood vessel contour setting unit configured to set a provisional blood vessel contour, based on a blood flow region determined by the blood flow region determination unit; and a blood vessel contour extraction unit configured to extract, using the provisional blood vessel contour set by the provisional blood vessel contour setting unit, a contour of the target blood vessel in the tomographic image generated by the tomographic image generation unit.

With this, the ultrasound diagnostic apparatus can trace, on the ultrasound image, the contour of the blood vessel wall of the target blood vessel detected by the blood flow region determination unit.

For example, the ultrasound diagnostic apparatus further includes: a probe position and orientation obtainment unit configured to obtain position and orientation information indicating at least one of a position and an orientation of the ultrasound probe; and a three-dimensional blood flow construction unit configured to generate three-dimensional blood flow information indicating the blood flow region in a three-dimensional space, based on (i) the position and orientation information obtained by the probe position and orientation obtainment unit and (ii) the blood flow information generated by the blood flow information generation unit, wherein the blood flow region determination unit is configured to perform the determination by analyzing the three-dimensional blood flow information generated by the three-dimensional blood flow construction unit.

With this, the ultrasound diagnostic apparatus can detect the target blood vessel based on the shape of the blood flow region in the three-dimensional space.

For example, the target blood vessel is a carotid artery.

With this, the ultrasound diagnostic apparatus can detect the carotid artery.

A blood vessel extraction method according to an exemplary embodiment disclosed herein is a blood vessel detection method in which a target blood vessel of a subject is detected based on reflected ultrasound waves obtained, using an ultrasound probe, from the subject, the blood vessel detection method including: generating a tomographic image of the subject, based on the reflected ultrasound waves; generating blood flow information indicating a blood flow region of the subject in the tomographic image, based on the reflected ultrasound waves; and determining whether or not the blood flow region corresponds to the target blood vessel, by analyzing the blood flow information generated in the generating of blood flow information.

With this, similar advantageous effects as the above-described ultrasound diagnostic apparatus are produced.

These general and specific aspects may be implemented using a system, a method, an integrated circuit, a computer program, or a computer-readable recording medium, such as a CD-ROM or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

Figure 12:
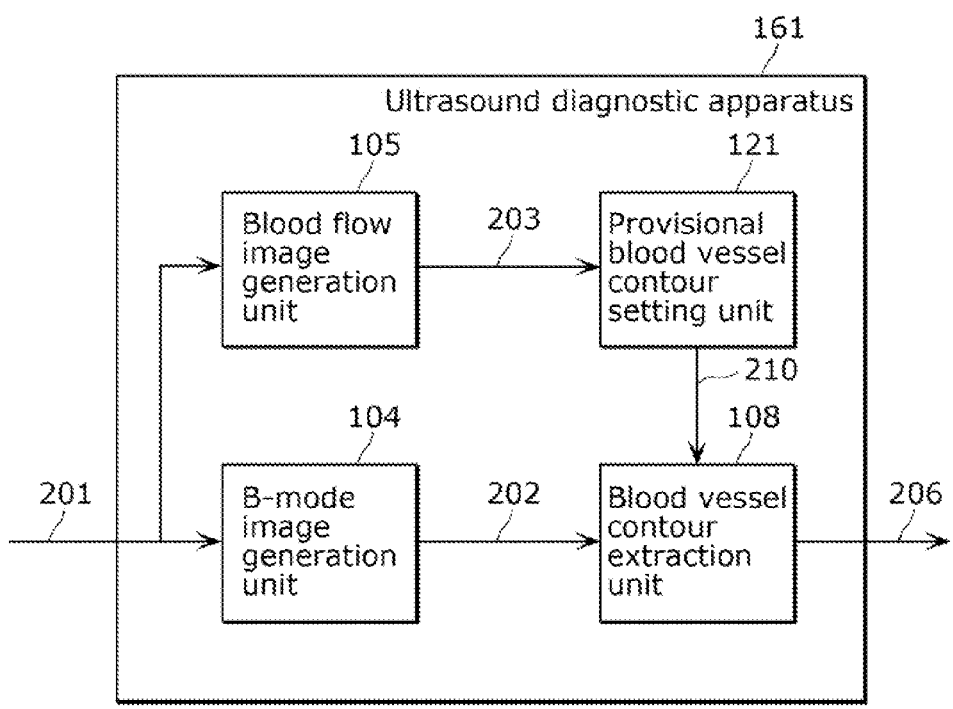
FIG. 12 is a diagram showing a second example of an assumed ultrasound diagnostic apparatus.

With purposes of reducing the burden on the examiner by reducing the trouble of manual tasks, and shortening the examination time, conventionally, there is a method in which a provisional blood vessel wall contour is set based on a position where blood flow information is present, and automatically extract a blood vessel wall contour using, as an initial contour, the provisional blood vessel wall contour that has been set (FIG. 12). However, there is a problem that extracting only a blood vessel of interest to be examined (hereinafter, also referred to as a target blood vessel or a blood vessel of interest) (e.g., a carotid artery) is difficult when various blood flow information is present.

For example, when a blood vessel other than a carotid artery (e.g., a jugular vein or a vertebral artery) is present in a measurement range, blood flow is present in the position corresponding to such a blood vessel. Thus, such a blood vessel can be extracted in error. Furthermore, a motion of tissue and so on can be observed as the blood flow information in error (a blood flow noise). As described, there is a problem that it is difficult to reliably extract only the target blood vessel.

Figure 1:
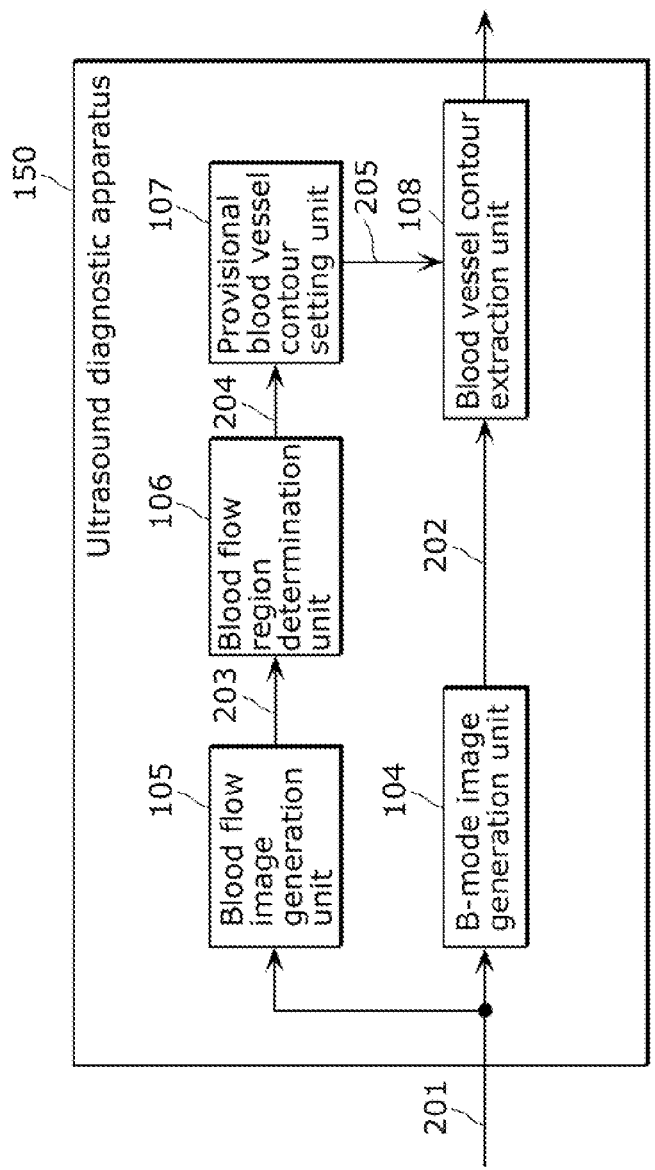
FIG. 1 is a diagram showing an outline configuration of an ultrasound diagnostic apparatus according to Embodiment 1.

An outline configuration of the ultrasound diagnostic apparatus according to this embodiment is described. FIG. 1 is a block diagram showing an outline configuration of an ultrasound diagnostic apparatus 150 according to this embodiment.

The ultrasound diagnostic apparatus 150 shown in FIG. 1 detects a target blood vessel based on reflected ultrasound waves 201 obtained from a subject by using an ultrasound probe. Note that, descriptions are given exemplifying the case in which an examiner linearly moves the ultrasound probe on the subject to sequentially obtain the reflected ultrasound waves. However, it should be noted that the movement of the ultrasound probe is not limited to linear movement. More specifically, the descriptions are also applicable to the case in which an operator moves the ultrasound probe curvilinearly.

The ultrasound diagnostic apparatus 150 includes: a B-mode image generation unit 104, a blood flow image generation unit 105, a blood flow region determination unit 106, a provisional blood vessel contour setting unit 107, and a blood vessel contour extraction unit 108.

The B-mode image generation unit 104 generates a B-mode image 202 based on the reflected ultrasound waves 201.

The blood flow image generation unit 105 corresponds to a blood flow information generation unit. The blood flow image generation unit 105 generates a blood flow image 203 showing a region including blood flow, based on the reflected ultrasound waves 201. The blood flow image 203 corresponds to blood flow information. Hereinafter, description is given using the blood flow image 203 as a specific example of the blood flow information. However, the blood flow information is not limited to the blood flow image 203. The blood flow information may be any information which indicates a region including blood flow in a subject.

The blood flow region determination unit 106 extracts a blood flow region 204 of a target blood vessel based on the blood flow image 203.

The provisional blood vessel contour setting unit 107 sets a provisional blood vessel contour 205 based on the blood flow region 204.

With the provisional blood vessel contour 205 as an initial contour, the blood vessel contour extraction unit 108 extracts an blood vessel contour (an adventitia contour of a blood vessel) 206 using the B-mode image 202. More specifically, for example, the blood vessel contour extraction unit 108 extracts the blood vessel contour 206 by performing, on the B-mode image 202, searching using the provisional blood vessel contour 205 as an initial contour.

The following describes details of the configuration of the ultrasound diagnostic apparatus 150 according to this embodiment.

Figure 2:
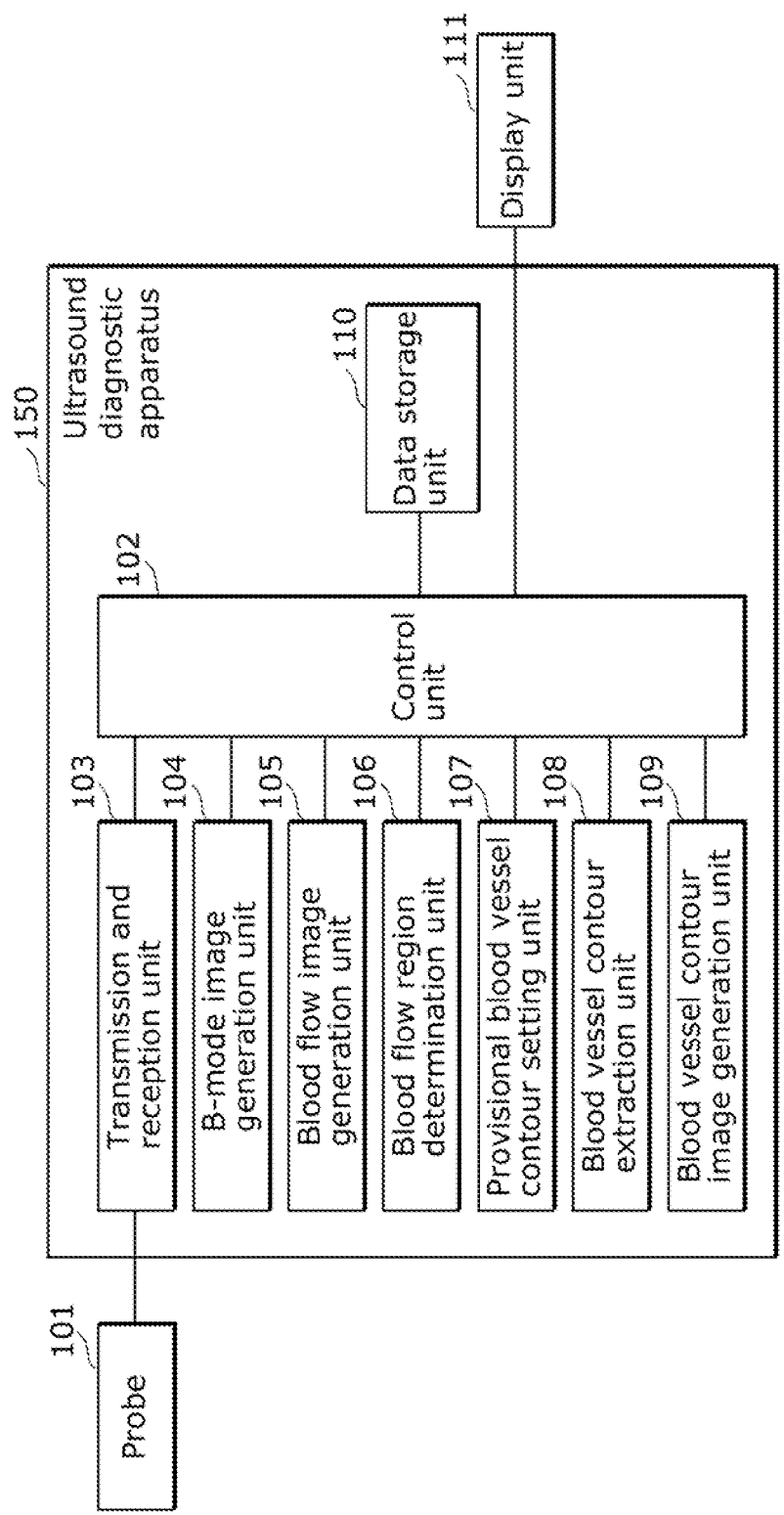
FIG. 2 is a block diagram showing a detailed configuration of the ultrasound diagnostic apparatus according to Embodiment 1.

FIG. 2 is a block diagram showing a detailed configuration of the ultrasound diagnostic apparatus 150 according to this embodiment.

The ultrasound diagnostic apparatus 150 shown in FIG. 2 includes: a control unit 102, a transmission and reception unit 103, the B-mode image generation unit 104, the blood flow image generation unit 105, the blood flow region determination unit 106, the provisional blood vessel contour setting unit 107, the blood vessel contour extraction unit 108, a blood vessel contour image generation unit 109, and a data storage unit 110. Furthermore, a probe 101 and a display unit 111 are provided outside the ultrasound diagnostic apparatus 150 and are connected to the ultrasound diagnostic apparatus 150. Note that, the probe 101 and the display unit 111 may be included in the ultrasound diagnostic apparatus 150. Furthermore, the probe 101 and the display unit 111 do not need to be included.

The probe 101 is an ultrasound probe including ultrasound transducers which transmit and receive ultrasound waves. The probe 101 transmits and receives ultrasound waves according to the instructions of the transmission and reception unit 103. Furthermore, the probe 101 receives, as echo signals, the reflected ultrasound waves 201 (ultrasound reflected signals) from the subject. It should be noted that the probe 101 may be a probe in which the ultrasound transducers are arranged in a one-dimensional direction, or a two-dimensional array probe in which the ultrasound transducers are arranged in a matrix.

The control unit 102 controls the respective processing units included in the ultrasound diagnostic apparatus 150. Hereinafter, although not specifically stated, the operations of the respective processing units are governed by the control unit 102. For example, the control unit 102 causes the respective processing units to execute the corresponding processing while the control unit 102 controls the operation timing, etc.

The transmission and reception unit 103 drives the ultrasound transducers of the probe 101 to cause the generation of ultrasound waves. Furthermore, the transmission and reception unit 103 receives the reflected ultrasound waves 201 received by the probe 101 from the subject.

The B-mode image generation unit 104 generates the B-mode image 202 based on the reflected ultrasound waves 201 received by the transmission and reception unit 103. Specifically, after performing filtering processing on the reflected ultrasound waves 201, the B-mode image generation unit 104 performs envelope detection. In addition, the B-mode image generation unit 104 generates the B-mode image 202 by performing logarithmic conversion and gain adjustment on the signal obtained as a result of the envelope detection.

The blood flow image generation unit 105 generates the blood flow image 203 based on the reflected ultrasound waves 201 received by the transmission and reception unit 103. Here, the blood flow image 203 is an image showing a region in which blood flows. Specifically, the blood flow image generation unit 105 detects the speed of the blood flow (blood flow speed) within the blood vessel using the frequency change caused by the ultrasound waves being reflected off the blood flow. Then, the blood flow image generation unit 105 generates the blood flow image 203 by representing the detected blood flow speed as color data in an image. It should be noted that the color Doppler method or power Doppler method can be used, for example, as a method of imaging blood flow speed.

The blood flow region determination unit 106 extracts the blood flow region 204 of a blood vessel of interest, based on the blood flow image generated by the blood flow image generation unit 105.

Note that, although the blood flow image generation unit 105 generates the blood flow image 203 here, the blood flow image generation unit 105 need not necessarily generate image. Specifically, the blood flow image generation unit 105 may generate information (blood flow information) indicating a region including blood flow, and the blood flow region determination unit 106 may extract the blood flow region 204 of the blood vessel of interest by using the blood flow information. The method for determining the blood flow region shall be described later in detail.

The provisional blood vessel contour setting unit 107 sets the provisional blood vessel contour 205, based on the blood flow region 204 extracted by the blood flow region determination unit 106. Then, the provisional blood vessel contour setting unit 107 transmits provisional blood vessel contour information indicating the set provisional blood vessel contour 205 to the blood vessel contour extraction unit 108.

After setting the provisional blood vessel contour 205 indicated by the provisional blood vessel contour information in the B-mode image 202, the blood vessel contour extraction unit 108 uses the provisional blood vessel contour 205 as an initial contour to extract, from the B-mode image 202, information indicating the blood vessel contour 206 which is more detailed. Here, the blood vessel contour extraction unit 108 extracts a contour which corresponds to a contour of adventitia of a blood vessel (adventitia contour).

Note that, although the blood vessel contour extraction unit 108 performs extraction from the B-mode image to extract the adventitia contour in this embodiment, the provisional blood vessel contour information may be set in the blood flow image 203 and then a lumen contour may be extracted from the blood flow image 203. Furthermore, both of the above may be performed to extract the adventitia contour and the lumen contour.

The blood vessel contour image generation unit 109 combines the information indicating the blood vessel contour extracted by the blood vessel contour extraction unit 108 to overlap the B-mode image 202, and thus generates a blood vessel contour image.

The data storage unit 110 stores the B-mode image 202 generated by the B-mode image generation unit 104, the blood flow image 203 generated by the blood flow image generation unit 105, and the blood vessel contour 206 generated by the blood vessel contour extraction unit 108.

The display unit 111 displays the B-mode image 202, the blood flow image 203, the blood vessel contour 206, or a piece of data thereof. The display unit 111 is a display device, such as a liquid crystal display (LCD). It should be noted that this embodiment is characterized by the contour extraction method for more accurately obtaining the contour of the blood vessel of interest. Therefore, whether or not to provide the ultrasound diagnostic apparatus 150 with the blood vessel contour image generation unit 109 and the data storage unit 110 is arbitrary.

Figure 3:
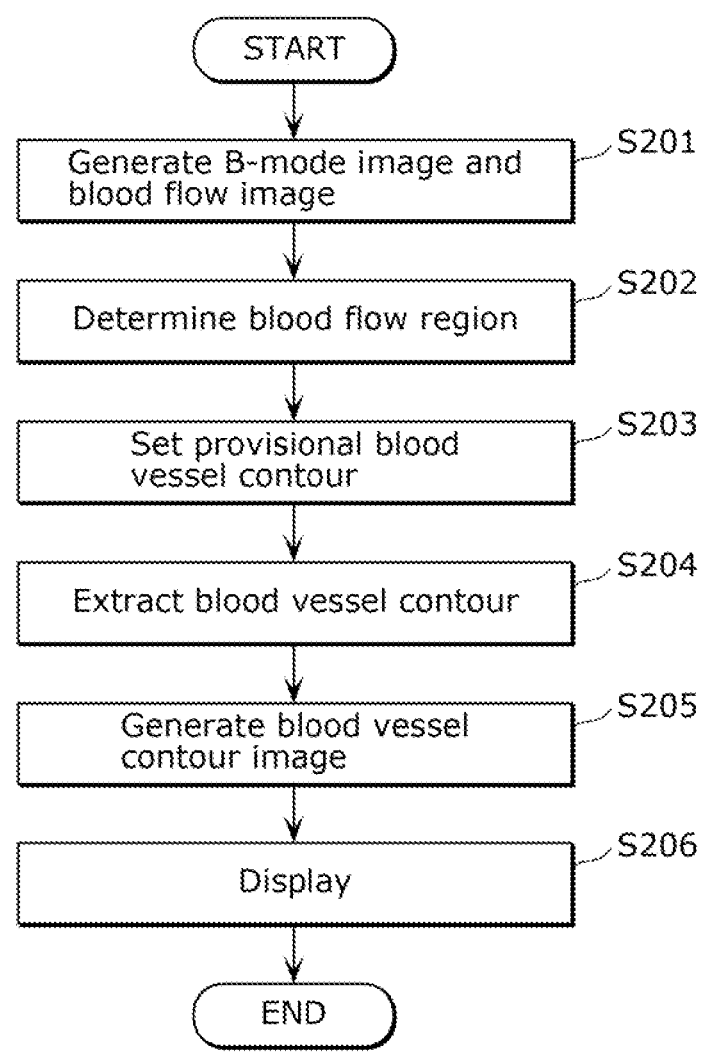
FIG. 3 is a first example of a flowchart showing extraction processing of a blood vessel contour performed by the ultrasound diagnostic apparatus according to Embodiment 1.

FIG. 3 is a first example of a flowchart showing extraction processing of the blood vessel contour 206 performed by the ultrasound diagnostic apparatus 150 according to this embodiment.

First, in step S201, the B-mode image generation unit 104 generates the B-mode image 202, and the blood flow image generation unit 105 generates the blood flow image 203. Specifically, the transmission and reception unit 103 emits ultrasound waves into the subject via the probe 101 and receives reflected ultrasound waves 201 via the probe 101. The B-mode image generation unit 104 and the blood flow image generation unit 105 respectively generate the B-mode image 202 and the blood flow image 203 by processing the data received by the transmission and reception unit 103, and store the generated B-mode image 202 and blood flow image 203 in the data storage unit 110. Note that, the generation of the B-mode image and the generation of the blood flow image may be performed sequentially in a time series (hereinafter, one generation unit of each of the B-mode image and the blood flow image is referred to as a frame for convenience).

Next, in step S202, the blood flow region determination unit 106 analyzes the blood flow image 203, and extracts the blood flow region 204 of the target blood vessel. This process is as follows.

In this embodiment, the blood flow region determination unit 106 initially extracts a blood flow region having an area larger than a predetermined value. The blood flow image 203 may include a small region (a region having a small area) that can be mistakenly judged as a blood flow region in a process of generating the blood flow image 203. Thus, with such a process, it is possible to efficiently remove a blood flow region other than the carotid artery from the blood flow image 203. Moreover, the blood flow region determination unit 106 calculates coordinates which indicate a position of the center of gravity of the blood flow region, and use the coordinates as a representative point (hereinafter referred to as a blood flow point) indicating the blood flow region. With the above, a blood flow point of a certain frame is extracted. Note that, there is a case where no blood flow point is extracted or a plurality of the blood flow points is extracted. Furthermore, although the position of the center of gravity of the blood flow region is used as the representative point here, a point indicated by the median values of the largest coordinates value and the smallest coordinates value of the blood flow region range may be used as the representative point. Moreover, as information of each of the blood flow points, a value indicating an area of the blood flow region may be calculated instead of the coordinates of the representative point. Furthermore, both of the above may be used together.

Figure 4:
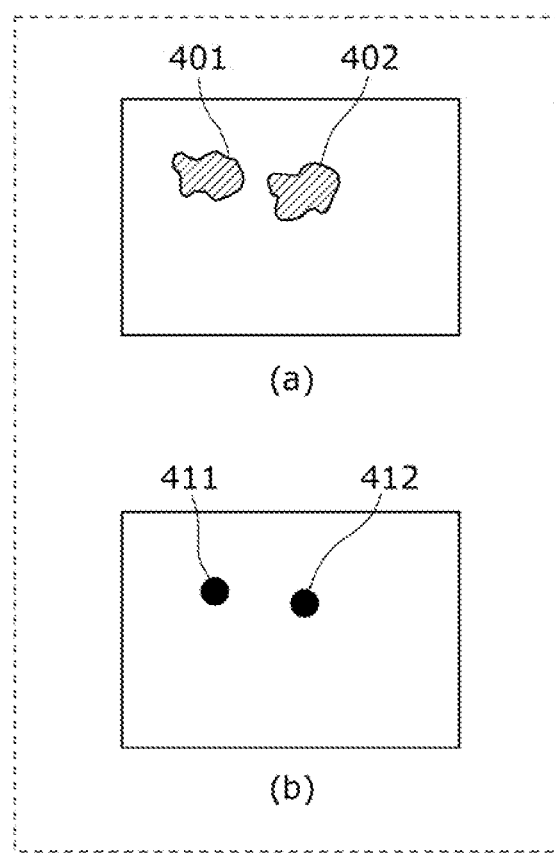
In FIG. 4, (a) is a diagram showing blood flow regions in a blood flow image, and (b) is a diagram showing blood flow points.

A process of extracting a blood flow point from the blood flow image is described with reference to FIG. 4. (a) in FIG. 4 is a diagram showing blood flow regions 401 and 402 in the blood flow image. (b) in FIG. 4 is a diagram showing blood flow points 411 and 412 corresponding to the blood flow regions 401 and 402, respectively. Here, the position of the center of gravity of the each of the blood flow regions is used as the respective blood flow points.

Next, the blood flow region determination unit 106 performs grouping of the blood flow points. The grouping of the blood flow points means that blood flow points which have a same feature are regarded as having a same label and put into a group. Note that, the label is an index for identifying a group. Any index, such as a name, a figure, a color, may be used as long as a group can be uniquely identified. In this embodiment, the blood flow region determination unit 106 groups blood flow points by assigning a blood flow point in a certain flame an identical figure (hereinafter referred to as a blood flow group number) as blood flow points representing blood flow at close positions in a plurality of frames before and after the certain frame. Note that, a collection of the grouped blood flow points may be referred to as a blood flow group.

More specifically, when a certain blood flow point in a certain frame is assumed to be a focused blood flow point, the blood flow region determination unit 106 focuses on a past frame obtained within one second from the obtainment of the certain frame. The blood flow region determination unit 106 assigns, to the focused blood flow point, a number same as the blood flow group number assigned to the past blood flow point, if a blood flow point, which is within a distance equivalent to 10 mm in a coordinate value with respect to the focused blood flow point, exists in the focused frame. Furthermore, when the blood flow point does not exist in the above-described range, the blood flow region determination unit 106 assigns, to the focused blood flow point, a new blood flow group number which has not been assigned before. The blood flow region determination unit 106 repeatedly applies this process to all of the obtained frames, and thus can assign all of the extracted blood flow points the blood flow group numbers. Thus, the blood flow region determination unit 106 can group all the blood flow points. Note that, the above-described "1 second" and "10 mm" are merely exemplary specific numerical values and may be a different time and a different length, respectively.

Next, the blood flow region determination unit 106 analyzes a blood flow point, and extracts a blood flow point which corresponds to the blood flow region of the target blood vessel. In this embodiment, analysis and extraction is performed on a blood flow group basis. The analysis here is, for example, a pattern matching. For example, the shape of the carotid artery which reaches the internal carotid artery and the external carotid artery from the common carotid artery is known to have a topographical feature of a Y-shape including a bifurcation. The blood flow region determination unit 106 extracts a set of blood flow groups which corresponds to such a topographical feature. The blood flow point belonging to the blood flow group extracted by the blood flow region determination unit 106 corresponds to the blood flow region 204 of the target blood vessel.

Figure 5:
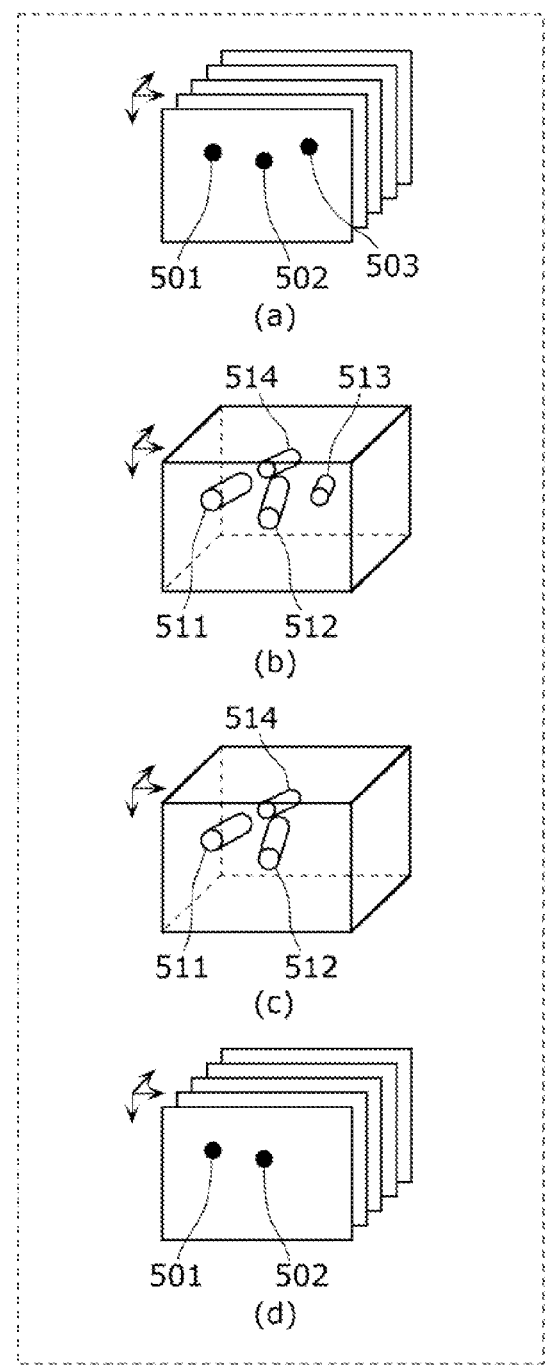
In FIG. 5, (a) is a diagram showing results of extraction of blood flow points in a plurality of frames, (b) is a diagram showing results of grouping of blood flow points, (c) is a diagram showing blood flow groups corresponding to blood flow regions of the extracted target blood vessels, and (d) is a diagram showing blood flow points corresponding to blood flow regions of the extracted target blood vessels.

FIG. 5 is an explanatory diagram which provides a schematic three-dimensional diagram in which a vertical axis and a horizontal axis are respectively assumed to be a vertical axis and a horizontal axis of each of the frames, and an axis in the depth direction is assumed to be an axis in the front-back direction of the frames (hereinafter referred to as a frame direction).

(a) in FIG. 5 shows results of extraction of blood flow points in each of the frames performed by the blood flow region determination unit 106. In (a) in FIG. 5, the frame disposed at the most front shows that three blood flow points 501, 502 and 503 are extracted. At this point, which of the blood flow points is the blood flow point corresponding to the target blood vessel is not known.

(b) in FIG. 5 is an example of results in which the blood flow points extracted as shown in (a) in FIG. 5 are grouped in the frame direction by the blood flow region determination unit 106. Each of the columns shown in (b) in FIG. 5 shows a collection of blood flow points having a same blood flow group number, and corresponds to the blood flow group. (b) in FIG. 5 includes four blood flow groups 511, 512, 513 and 514. The blood flow region determination unit 106 performs, when the target blood vessel is a carotid artery, pattern matching using as a reference pattern, for example, a pattern having a V-shape feature. This pattern matching makes it possible to select ((c) in FIG. 5), from among the four blood flow groups shown in (a) in FIG. 5, the blood flow groups 511, 512 and 514 having a feature similar to the reference pattern. As a result, the blood flow region determination unit 106 can extract, as the blood flow region of the target blood vessel, the blood flow points belonging to the blood flow groups 511, 512 and 514.

(d) in FIG. 5 shows that blood flow points 501 and 502 are extracted as target blood flow regions. The blood flow point 503 extracted by the blood flow region determination unit 106 in (a) in FIG. 5 belongs to the blood flow group 513, and thus is judged not to correspond to the target blood vessel and is appropriately removed.

Note that, although an example in which the blood flow region determination unit 106 uses a pattern matching technique is described here, an extraction method based on the machine learning may be adopted in which a feature of the target blood vessel is learnt. Furthermore, the blood flow region determination unit 106 may use not only a topographical feature formed due to positional relationship between the groups, but may also use information such as a blood flow area. For example, at a bifurcation of a carotid artery, the area of the blood flow region tends to be significantly large. Thus, the blood flow region determination unit 106 may, after obtaining a blood flow point associated with a blood flow region having a largest area in each of the groups, judge that the group, among the groups, having the largest blood flow area is the region including the bifurcation, and extract such a group. Moreover, the blood flow region determination unit 106 may, after extracting the blood flow group including the bifurcation, further extract a plurality of blood flow groups based on a positional relationship with respect to the extracted blood flow group. With this, the blood flow group which is used as a reference is determined early, and thus the target blood flow group can be extracted more efficiently.

Another example is that the blood flow region determination unit 106 may extract a blood flow group of the target blood vessel, based on a blood flow area using a feature of a pulsation-like change in the area. Generally, an artery has a larger change in a blood vessel diameter, and thus has a feature that the change in the blood flow area is large. Use of such a feature enables the blood flow region determination unit 106 to extract the target blood vessel more appropriately, when an artery and a vein are meant to be distinguished.

Furthermore, the blood flow region determination unit 106 may analyze the blood flow group itself, before performing processing, such as pattern matching. For example, blood flow noises are often drawn intermittently in the frame direction, and are sometimes separated into individual groups including a small number of blood flow points. Thus, among the blood flow groups, a blood flow group including a smaller number of blood flow points than a threshold value may be judged to be a blood flow noise, and an analysis thereafter on such a blood flow group may be omitted. With this, the need to perform processing of unnecessary information is eliminated, and thus the target blood flow group can be extracted more efficiently.

Referring back to FIG. 3, next, in step S203, the provisional blood vessel contour setting unit 107 sets the provisional blood vessel contour 205 based on the blood flow region 204 of the target blood vessel extracted in step S202. The blood vessel contour is assumed to exist in a periphery of the extracted target blood flow region, and thus a provisional blood vessel contour is set in a position of the blood flow region 204 of the target blood vessel. In this embodiment, a provisional blood vessel contour is set to have a circular shape, assuming that a blood vessel image in a circular shape is obtained by scanning a probe to allow an image which cuts the blood vessel in round slices to be drawn.

First, the provisional blood vessel contour setting unit 107 determines for each frame whether or not a blood flow point which corresponds to the target blood flow region exists. When a blood flow point corresponding to the target blood flow region exists, the provisional blood vessel contour setting unit 107 sets, as a provisional blood vessel contour, a circle having the blood flow point as a center. At this time, it is desirable that the provisional blood vessel contour setting unit 107 determine a radius of the circle to allow the circle, which is set as the provisional blood vessel contour, to include the target blood flow region. Furthermore, the provisional blood vessel contour setting unit 107 may determine a radius of the circle based on a statistical average value of a radius of the blood vessel of interest.

In step S204, the blood vessel contour extraction unit 108 extracts the blood vessel contour 206 from the B-mode image 202, based on the provisional blood vessel contour 205 set in step S203. In this embodiment, the blood vessel contour extraction unit 108 determines, as the blood vessel contour 206, a contour that is obtained as a result of performing the active contour searching (Snakes, and so on) on the B-mode image 202 using a provisional blood vessel contour as an initial contour. Here, the active contour searching is processing for extracting a contour by moving the contour points of the initial contour by performing energy minimization. In the Snakes algorithm, the contour is determined to minimize energy $E_{snakes}$ defined in, for example, (Equation 1), (Equation 2), and (Equation 3), $$E_{snakes} = \alpha E_{int} + \beta E_{image} \quad \text{(Equation 1)}$$

$$E_{int} = (w_1 |v_s|^2 + w_2 |v_{ss}|^2)/2 \quad \text{(Equation 2)}$$

$$E_{image} = -(G_\sigma * \nabla^2 I)^2 \quad \text{(Equation 3)}$$

Here, $E_{int}$ is the inner deformation energy of the contour line, and $E_{image}$ is the image energy representing the conformity between the contour line and the image. v denotes a parameter expression of the contour line, $v_s$ denotes a first order differential of v, and $v_{ss}$ denotes a second order differential of v. $\alpha$, $\beta$, $w_1$, and $w_2$ denote constants indicating weight. Gσ denotes a Gaussian filter, $\nabla^2$ denotes a Laplacian filter, "*" denotes an operator of convolution, and I denotes the brightness value of the image. More specifically, the Snakes algorithm represents the contour line as contour points obtained by discretization of the contour line, and determines, for each contour point, a point such that energy $E_{snakes}$ is minimized. For example, by setting α=0.8, and β=0.2, it is possible to search for the contour while maintaining the original circular shape.

In step S205, the blood vessel contour image generation unit 109 generates a blood vessel contour image by overlapping information indicating a blood vessel contour onto the B-mode image.

In step S206, the display unit 111 displays the generated image.

Noted that, as described earlier, the adoption of step S205 (a blood vessel contour image generation step) and step S206 (a display step) is arbitrary.

Figure 6:
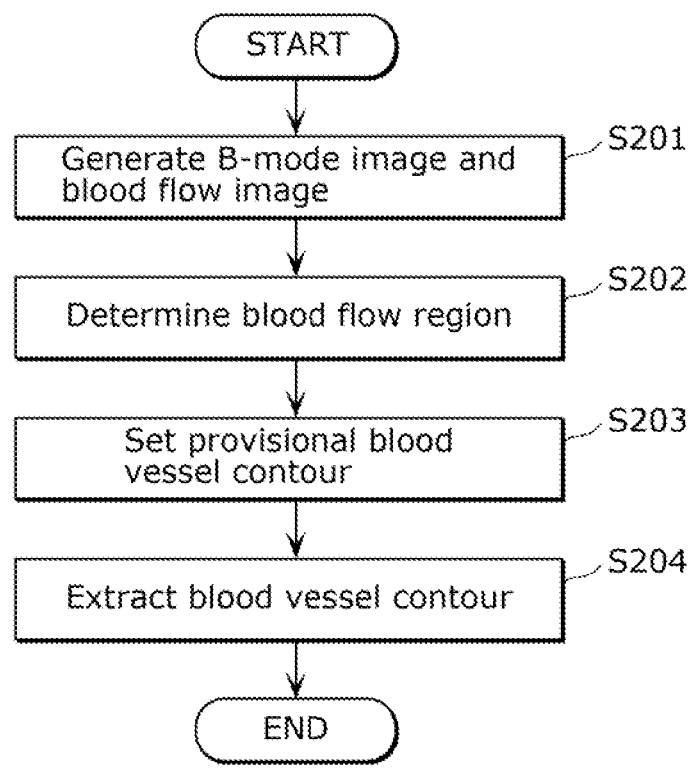
FIG. 6 is a second example of a flowchart showing extraction processing of a blood vessel contour performed by the ultrasound diagnostic apparatus according to Embodiment 1.

FIG. 6 is a second example of a flowchart showing extraction processing of the blood vessel contour 206 performed by the ultrasound diagnostic apparatus 150 according to this embodiment. As shown in FIG. 6, the ultrasound diagnostic apparatus 150 may perform just the processing in steps S201 to S204.

With the above, the ultrasound diagnostic apparatus 150 according to this embodiment obtains the blood flow region of the target blood vessel based on the distribution of the blood flow region, and extract the contour of the target blood vessel based on the blood flow region. With this, the ultrasound diagnostic apparatus 150 can obtain contour position information more stably and more accurately. As a result, the ultrasound diagnostic apparatus 150 can correctly trace the contour of the blood vessel wall to be extracted.

Embodiment 2

This embodiment describes an example of an ultrasound diagnostic apparatus which can extract the shape of a target blood vessel more accurately by using information indicating at least one of a position and an orientation of the probe.

Figure 7:
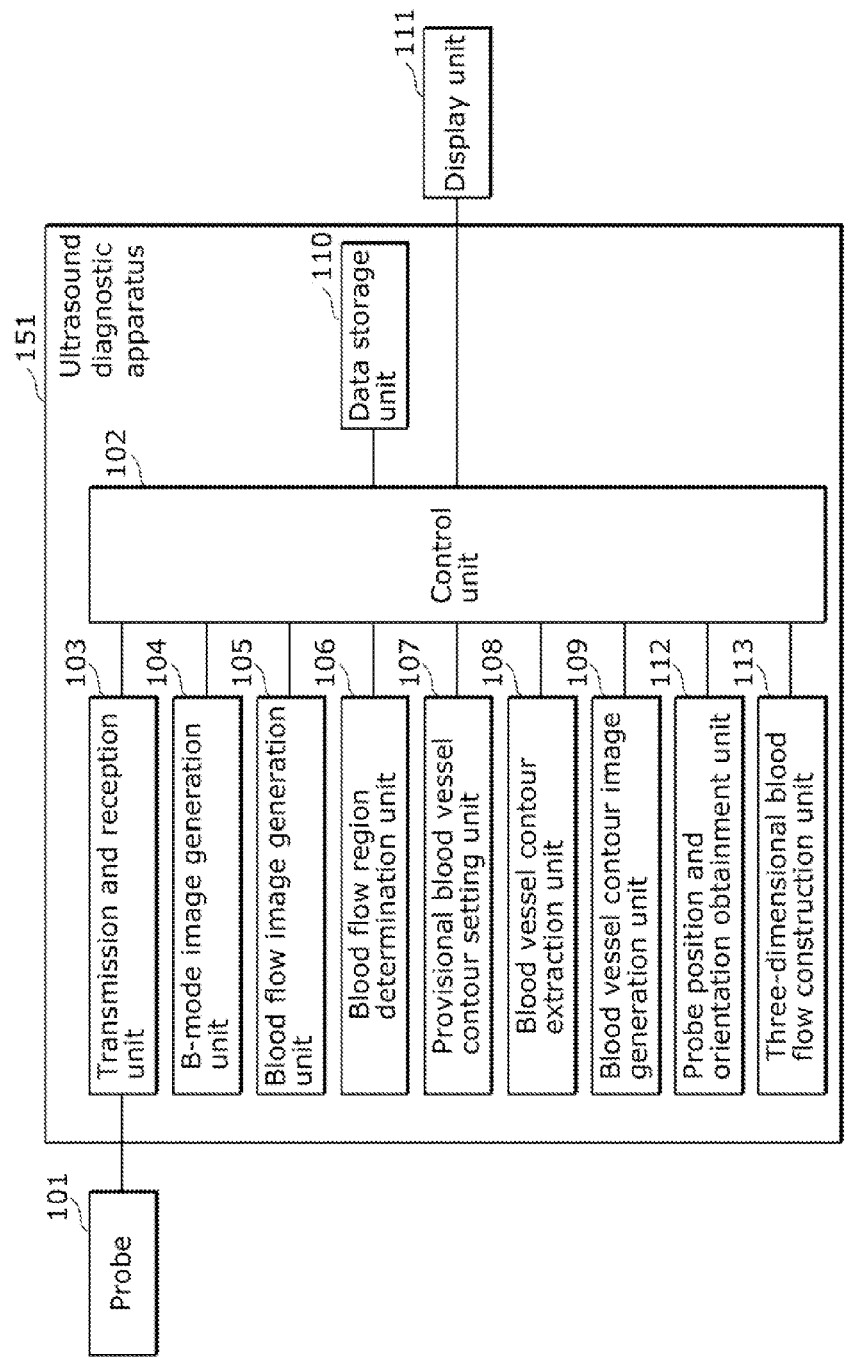
FIG. 7 is a block diagram showing an outline configuration of an ultrasound diagnostic apparatus according to Embodiment 2.

FIG. 7 is a block diagram showing an outline configuration of an ultrasound diagnostic apparatus 151 according to this embodiment. Note that, in FIG. 7, structural elements that are the same as those in FIG. 2 use the same reference numerals, and their description shall not be repeated.

The ultrasound diagnostic apparatus 151 shown in FIG. 7 includes, in addition to the configuration of an ultrasound diagnostic apparatus 150 shown in FIG. 2, a probe position and orientation obtainment unit 112, and a three-dimensional blood flow construction unit 113.

The probe position and orientation obtainment unit 112 obtains position and orientation information indicating at least one of a position and an orientation of a probe 101.

The three-dimensional blood flow construction unit 113 generates, based on (i) position and orientation information of the probe 101 and (ii) the blood flow image 203, three-dimensional blood flow information which indicates blood flow information in a three-dimensional space.

The ultrasound diagnostic apparatus 150 according to Embodiment 1 identifies a blood flow region corresponding to a target blood vessel, by analyzing a topographical feature of blood flow points. When a blood vessel is scanned by moving a probe irregularly, the irregular movement of the probe can be unintentionally reflected in the topographical feature of the blood flow point. In particular, the effect of the irregular movement of the probe in a direction along the running direction of the blood vessel is large. For example, the shape of the extracted blood flow points is a shape obtained by connecting two Y-shapes, in the case where a probe is moved along the running direction of the blood vessel, from the common carotid artery to the internal carotid artery and the external carotid artery, to obtain the drawing, and then the motion of the probe is reversed, that is, the probe is moved toward the common carotid artery from the internal carotid artery and the external carotid artery. In other words, the extracted blood flow points do not form a Y-shape which correctly shows the shape of the carotid artery. Thus, it is difficult to capture a topographical feature of the carotid artery from the shape in which the movement of the probe is reflected, and thus the target blood vessel cannot be extracted correctly.

In view of this, the ultrasound diagnostic apparatus 151 according to this embodiment obtains the position and orientation information of the probe to remove the effect of movement of the probe. Then, the three-dimensional blood flow information is generated based on the obtained position and orientation information. Moreover, based on the generated blood flow information, blood flow is analyzed in a similar manner as Embodiment 1.

With this configuration, even when the probe is moved irregularly, it is possible to reduce effect on the blood flow of the target blood vessel other than the blood flow information. Thus, the position of a blood vessel to be extracted can be obtained more accurately.

Embodiment 3

In this embodiment, a modification of the above-described Embodiment 1 shall be described.

Figure 8:
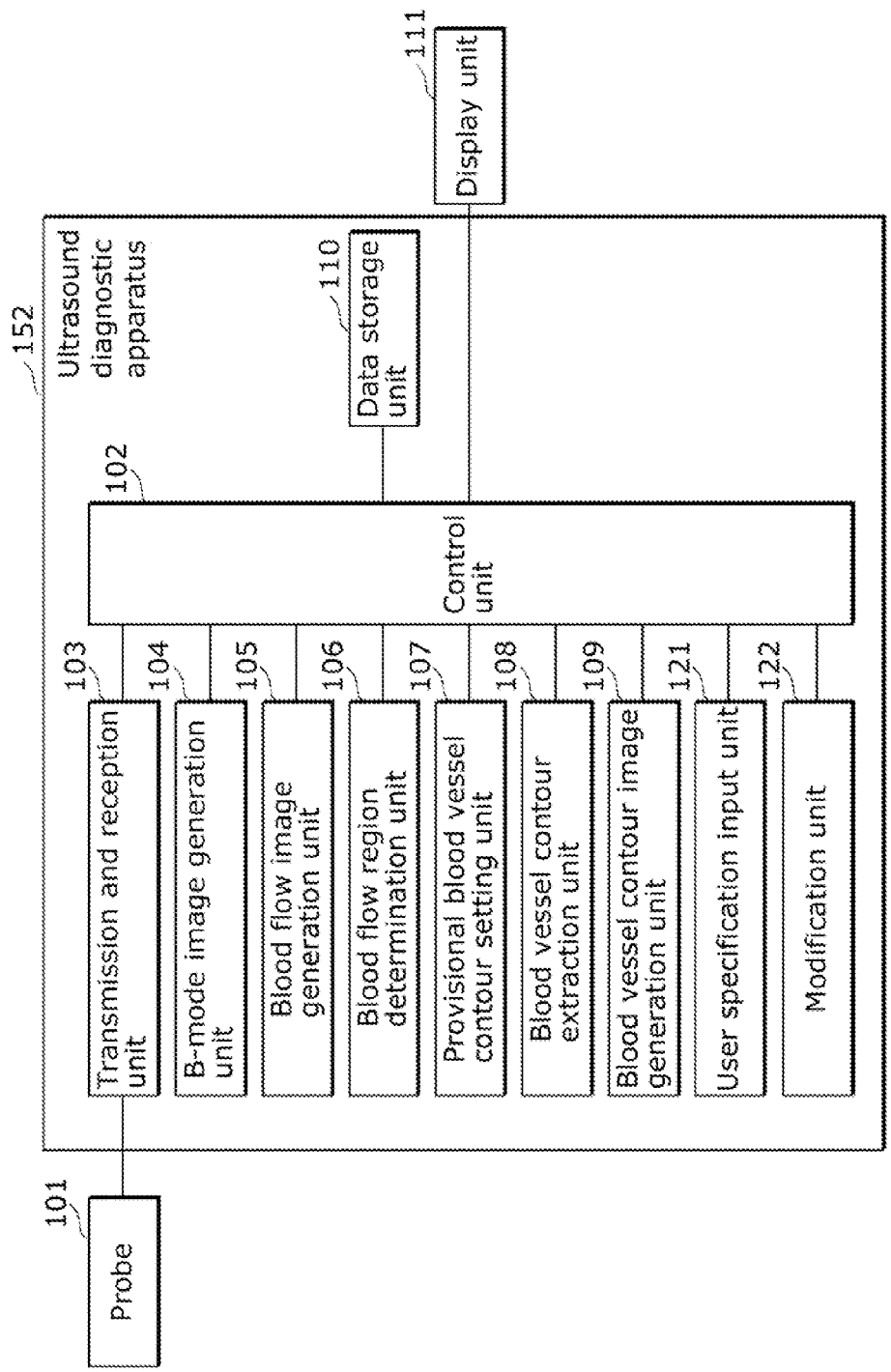
FIG. 8 is a block diagram showing an outline configuration of an ultrasound diagnostic apparatus according to Embodiment 3.

FIG. 8 is a block diagram showing a configuration of an ultrasound diagnostic apparatus 152 according to this embodiment. It should be noted that, in FIG. 8, structural elements that are the same as those in FIG. 2 use the same reference numerals, and their description shall not be repeated.

The ultrasound diagnostic apparatus 152 shown in FIG. 8 includes, in addition to the configuration of an ultrasound diagnostic apparatus 150 shown in FIG. 2, a user specification input unit 121 and a modification unit 122.

The user specification input unit 121 receives a request for modification from a user.

The modification unit 122 modifies, based on the request for modification received by the user specification input unit 121, a blood flow region determination result obtained by a blood flow region determination unit 106.

Figure 9:
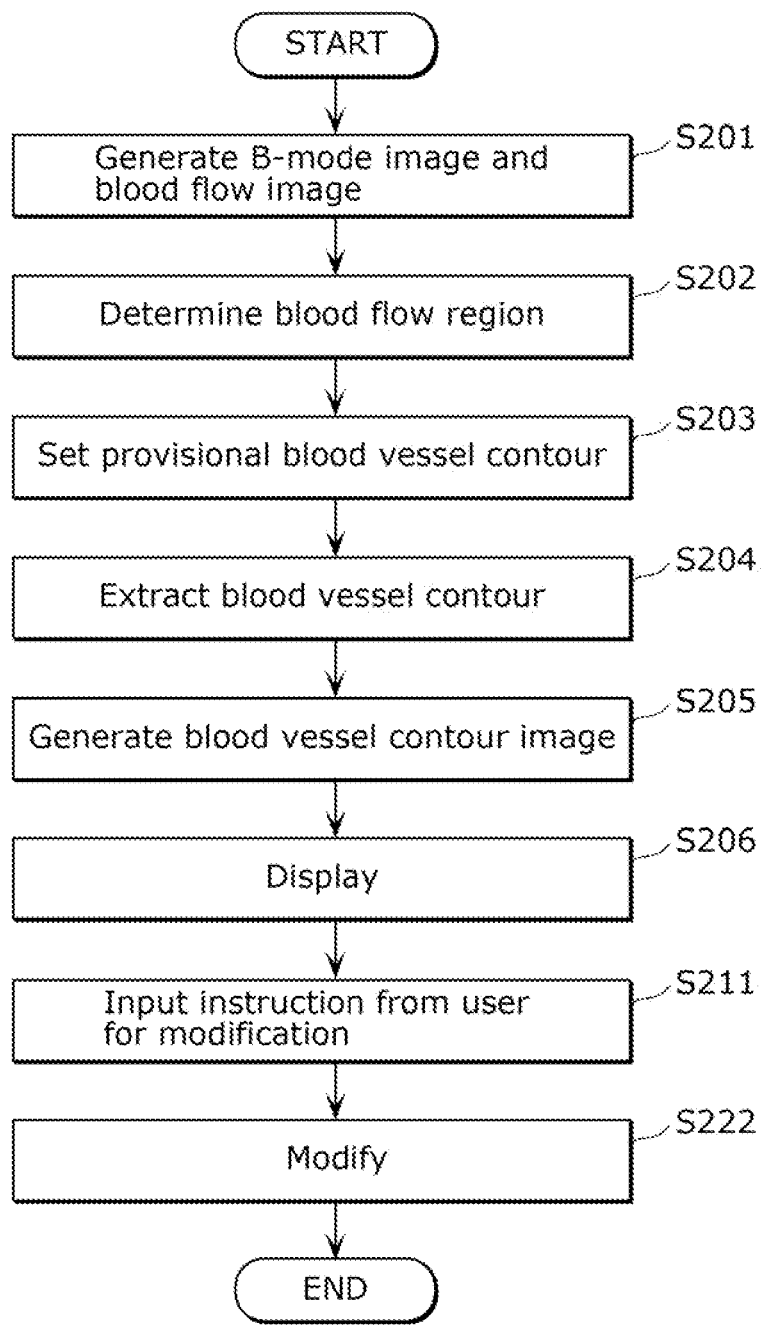
FIG. 9 is a flowchart showing extraction processing of a blood vessel contour performed by the ultrasound diagnostic apparatus according to Embodiment 3.

FIG. 9 is a flowchart of extraction processing of a blood vessel contour performed by the ultrasound diagnostic apparatus 152 according to this embodiment.

In a similar manner as Embodiment 1, the ultrasound diagnostic apparatus 152 performs processes shown in step S201 to step S206.

Next, in step S211, the user specification input unit 121 receives a request for modification from a user.

Next, in step S222, the modification unit 122 modifies, based on the request for modification received by the user specification input unit 121, a blood flow region determination result obtained by the blood flow region determination unit 106.

Embodiment 1 identifies a blood flow region corresponding to the target blood vessel by analyzing a topographical feature of blood flow points, and has a problem that the target blood vessel cannot be correctly extracted, when the analysis result is erroneous. For example, when blood flow of a jugular vein is identified as the target blood flow in error, a blood vessel wall of the jugular vein is extracted. As described, when an analysis is erroneous, the target blood vessel cannot be correctly extracted.

Thus, in order to extract the target blood vessel correctly even when the analysis is erroneous, a unit is provided for inputting an instruction from a user for modification, and the blood flow region determination result is modified based on the inputted instruction for modification. Moreover, based on the modified blood flow region determination result, a provisional blood vessel contour is set, a blood vessel contour is extracted, and a blood vessel contour image is generated in a similar manner as Embodiment 1.

The user provides instruction for modification, for example, on a blood flow group basis. In such a case, selection or de-selection of the blood flow group is instructed. More specifically, when a wrong blood flow group is selected as the target blood flow region, de-selection is instructed. In response, the target blood flow region modification unit modifies the target blood flow region to remove the wrong blood flow group from the target blood flow region. Furthermore, selection of the blood flow group which has not been extracted as the target blood flow region is instructed. In response, the target blood flow region modification unit modifies the target blood flow region to extract such a blood flow group as the target blood flow region.

Note that, the modification of the target blood flow region by the target blood flow region modification unit need not necessarily on the blood flow group basis.

With this configuration, it becomes possible to modify an error, even when the analysis of the blood flow image is difficult and thus the target blood flow region is extracted in error. Thus, the judgment by the user is reflected, and a blood vessel to be extracted can be extracted more accurately.

Figure 10:
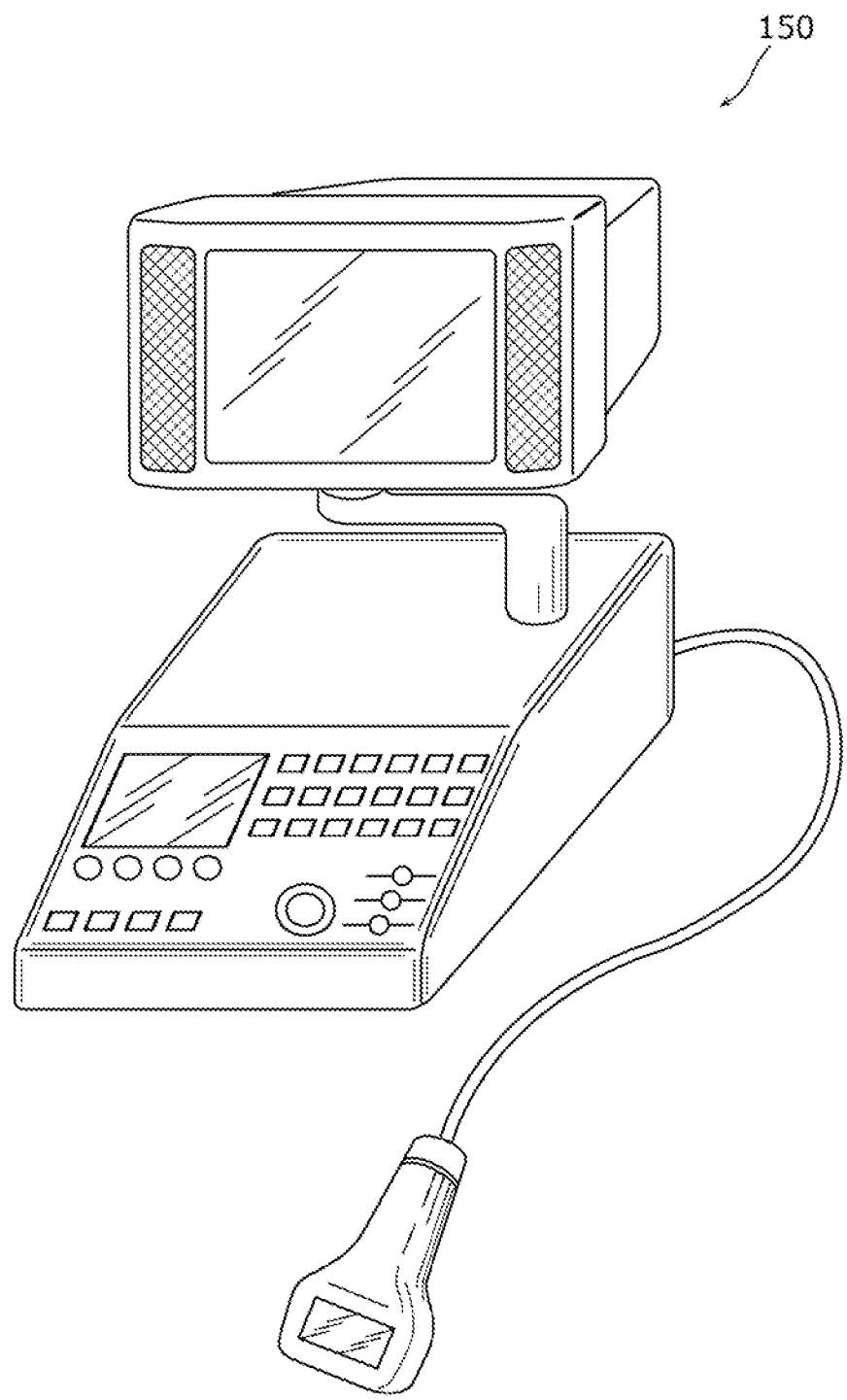
FIG. 10 is an external view of an ultrasound diagnostic apparatus according to each of the embodiments.

The ultrasound diagnostic apparatuses according to the embodiments have been described thus far. The appearance of the ultrasound diagnostic apparatus according to each of the embodiments is shown in FIG. 10, for example.

Note that, the herein disclosed subject matter is not Limited to the above-described embodiments. For example, part or all of the processing units included in the ultrasound diagnostic apparatus in the above-described embodiments may be included in the probe 101.

Furthermore, although description in each of the embodiments is carried out exemplifying the case of using, as the B-mode image and the blood flow image, what is called a short axis view that is a blood vessel cross-section which is perpendicular to the running direction of the blood vessel, the one or more exemplary embodiments disclosed herein can also be applied to the case of using what is called a long axis view that is a blood vessel cross-section which is parallel to the running direction of the blood vessel. In such a case, the provisional blood vessel contour setting unit 107 determines a quadrangular provisional blood vessel contour. Here, quadrangular refers to a rectangle, a parallelogram, and an approximately rectangular shape.

Furthermore, each of the processing units included in the ultrasound diagnostic apparatus according to the above-described embodiments is typically implemented as an LSI which is an integrated circuit. These processing units may be individually configured as single chips or may be configured so that a part or all of the processing units are included in a single chip.

Furthermore, the method of circuit integration is not limited to LSIs, and implementation through a dedicated circuit or a general-purpose processor is also possible. A field programmable gate array (FPGA) which allows programming after LSI manufacturing or a reconfigurable processor which allows reconfiguration of the connections and settings of the circuit cells inside the LSI may also be used.

Furthermore, part or all of the functions of the ultrasound diagnostic apparatus, according to each of the embodiments may be implemented through the execution of a program by a processor, such as a CPU.

In addition, the present disclosure may be the aforementioned program or a non-transitory computer-readable recording medium on which such program is recorded. Furthermore, it should be obvious that the program can also be distributed via a transmission medium such as the Internet.

Furthermore, at least part of the functions of the ultrasound diagnostic apparatuses according to the embodiments and their modifications may be combined.

Furthermore, all the numerical figures used above are given as examples to describe the present disclosure in specific terms, and thus the present disclosure is not limited by such illustrative numerical figures.

Furthermore, the separation of the function blocks in the block diagrams is merely an example, and plural function blocks may be implemented as a single function block, a single function block may be separated into plural function blocks, or part of functions of a function block may be transferred to another function block. Furthermore, the functions of function blocks having similar functions may be processed, in parallel or by time-sharing, by a single hardware or software.

Furthermore, the sequence in which the above-described steps are executed is given as an example to describe the present disclosure in specific terms, and thus other sequences are possible. Furthermore, part of the above-described steps may be executed simultaneously (in parallel) with another step.

In addition, as long as they do not depart from the essence of the present disclosure, various modifications obtainable through modifications to the respective embodiments that may be conceived by a person of ordinary skill in the art are intended to be included in the present disclosure.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the ultrasound diagnostic apparatus according to each of the embodiments is a program described below.

The program causes a computer to execute a blood vessel identification method in which a blood vessel of interest of a subject is identified based on reflected ultrasound waves obtained, using an ultrasound probe, from the subject, the blood vessel identification method including: generating a tomographic image of the subject, based on the reflected ultrasound waves; generating blood flow information indicating a blood flow region of the subject in the tomographic image, based on the reflected ultrasound waves; and (i) extracting a blood flow point indicating a representative point of the blood flow region, (ii) extracting, as a group of blood flow regions, a plurality of the blood flow points having a same feature, and (iii) determining, on a group of blood flow regions basis, whether or not the blood flow region corresponds to the blood vessel of interest, by analyzing the blood flow information generated in the generating of blood flow information.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

An ultrasound diagnostic apparatus according to one or more exemplary embodiments disclosed herein has a unit for correctly obtaining the shape of a blood vessel wall, and is useful in the diagnosis of arteriosclerosis.

The invention claimed is:

1. An ultrasound diagnostic apparatus which identifies a blood vessel of interest of a subject based on reflected ultrasound waves obtained from the subject using an ultrasound probe, the ultrasound diagnostic apparatus comprising:
   a tomographic image generation unit configured to generate tomographic images of the subject based on the reflected ultrasound waves;
   a blood flow information generation unit configured to generate blood flow information of a plurality of frames indicating blood flow regions of the subject in the tomographic images based on the reflected ultrasound waves; and
   a blood flow region determination unit configured to:
   (i) analyze the blood flow information generated by the blood flow information generation unit,
   (ii) one of (a) extract blood flow points indicating representative points of the blood flow regions to calculate relative positions of the blood flow points across the plurality of frames and extract the blood flow points as a blood flow group, and (b) compare areas of the blood flow regions across the plurality of frames to extract the blood flow regions as the blood flow group, and
   (iii) determine, for each of a plurality of extracted blood flow groups, whether or not each blood flow region of the blood flow group corresponds to the blood vessel of interest based on at least one of relative positions of the plurality of blood flow groups, area information of the blood flow region, direction information of blood flow, and an attribute of the blood flow group.

2. The ultrasound diagnostic apparatus according to claim 1, wherein the blood flow region determination unit is configured to perform the determination by analyzing, as the blood flow information, positions of the blood flow regions in the tomographic images.

3. The ultrasound diagnostic apparatus according to claim 1, wherein when a plurality of the blood flow regions are arranged corresponding to respective positions on the subject at which the tomographic images have been obtained, the blood flow region determination unit is further configured to (i) collectively extract, as the blood flow group, from among the arranged blood flow regions, blood flow regions associated with blood blow points that are separated from one another by a distance no greater than a threshold value, and (ii) perform the determination on a blood flow region included in the extracted blood flow group, based on an attribute of the extracted blood flow group.

4. The ultrasound diagnostic apparatus according to claim 3, wherein when the attribute of the extracted blood flow group matches a predetermined attribute of the blood vessel of interest, the blood flow region determination unit is configured to perform the determination that the blood flow region included in the extracted blood flow group corresponds to the blood vessel of interest.

5. The ultrasound diagnostic apparatus according to claim 4, wherein the blood flow region determination unit is configured to perform the determination using, as the attribute of the extracted blood flow group, at least one of (i) a total number of blood flow regions included in the extracted blood flow group, (ii) an area of a blood flow region having a largest area, among the blood flow regions included in the extracted blood flow group, and (iii) a position of a blood flow region in each of tomographic images which are obtained at a beginning and at an end of a range on the subject in which a plurality of tomographic images including the extracted blood flow group are obtained.

6. The ultrasound diagnostic apparatus according to claim 5, wherein when the total number of the blood flow regions included in the extracted blood flow group is no greater than a predetermined number, the blood flow region determination unit is configured to perform the determination on a blood flow region included in another blood flow group other than the blood flow group which includes the blood flow regions the total number of which is no greater than the predetermined number.

7. The ultrasound diagnostic apparatus according to claim 5, wherein the blood flow region determination unit is configured to determine that a blood flow region included in a blood flow group, which is from among the plurality of the blood flow groups, and which includes a blood flow region having a largest area corresponds to the blood vessel of interest.

8. The ultrasound diagnostic apparatus according to claim 5, wherein when the plurality of the extracted blood flow groups are arranged corresponding to respective positions on the subject at which the tomographic images have been obtained, when a distance between (i) an edge of a drawing formed by an interpolation of a first blood flow group and (ii) a portion of a drawing formed by an interpolation of a second blood flow group is no greater than a predetermined value, the blood flow region determination unit is further configured to (i) newly and collectively extract, as a blood flow group, the first blood flow group and the second blood flow group and (ii) perform the determination on the newly and collectively extracted blood flow group.

9. The ultrasound diagnostic apparatus according to claim 5, wherein when the plurality of the extracted blood flow groups are arranged corresponding to respective positions on the subject at which the tomographic images have been obtained, (i) when a difference between a first position and a second position is no greater than a predetermined value, the first position being of a first blood flow region included in a tomographic image obtained at a beginning or at an end of a range on the subject corresponding to the extracted blood flow groups, and the second position being of a second blood flow region which is included in a tomographic image obtained at the beginning or at the end of the range on the subject and is different from the first blood flow region, and (ii) when a position on the subject at which the first blood flow region has been obtained and a position on the subject at which the second blood flow region has been obtained are within a predetermined distance, the blood flow region determination unit is further configured to newly and collectively extract, as a blood flow group, a blood flow group including the first blood flow region and a blood flow group including the second blood flow region, and perform the determination on the newly and collectively extracted blood flow group.

10. The ultrasound diagnostic apparatus according to claim 1, wherein the blood flow region determination unit is configured to perform the determination by analyzing, as the blood flow information, an area of each blood flow region in the tomographic images.

11. The ultrasound diagnostic apparatus according to claim 10, wherein the blood flow region determination unit is configured to perform the determination by determining the presence or absence of a pulsation-like fluctuation, by analyzing a change in area of the blood flow region in each of the obtained tomographic images.

12. The ultrasound diagnostic apparatus according to claim 1, wherein the blood flow region determination unit is configured to perform the determination by analyzing, as the blood flow information, the direction information of blood flow in the blood flow regions.

13. The ultrasound diagnostic apparatus according to claim 12, wherein the blood flow region determination unit is configured to perform the determination that the blood flow region corresponds to the blood vessel of interest, when a direction of the blood flow in the blood flow region matches a predetermined direction of blood flow in the blood vessel of interest.

14. The ultrasound diagnostic apparatus according to claim 1, further comprising:
   a display unit configured to display information indicating a result of the determination performed by the blood flow region determination unit; and
   a modification unit configured to modify the result of the determination performed by the blood flow region determination unit, based on a request from a user to modify the information indicating the result of the determination displayed on the display unit.

15. The ultrasound diagnostic apparatus according to claim 1, further comprising:
   a provisional blood vessel contour setting unit configured to set a provisional blood vessel contour, based on the determination performed by the blood flow region determination unit; and
   a blood vessel contour extraction unit configured to extract, using the provisional blood vessel contour set by the provisional blood vessel contour setting unit, a contour of the blood vessel of interest in a tomographic image generated by the tomographic image generation unit.

16. The ultrasound diagnostic apparatus according to claim 1, further comprising:
   a probe position and orientation obtainment unit configured to obtain position and orientation information indicating at least one of a position and an orientation of the ultrasound probe; and
   a three-dimensional blood flow construction unit configured to generate three-dimensional blood flow information indicating the blood flow region in a three-dimensional space, based on (i) the position and orientation information obtained by the probe position and orientation obtainment unit and (ii) the blood flow information generated by the blood flow information generation unit,
   wherein the blood flow region determination unit is configured to perform the determination by analyzing the three-dimensional blood flow information generated by the three-dimensional blood flow construction unit.

17. The ultrasound diagnostic apparatus according to claim 1, wherein the blood vessel of interest is a carotid artery.

18. The ultrasound diagnostic apparatus according to claim 1, wherein the blood flow determination unit determines whether or not each blood flow region corresponds to the blood vessel of interest by comparing the blood flow information to predetermined data related to said at least one of the relative positions of the plurality of blood flow groups, the area information of the blood flow region, the direction information of blood flow, and the attribute of the blood flow group.

19. A blood vessel identification method in which a blood vessel of interest of a subject is identified based on reflected ultrasound waves obtained from the subject using an ultrasound probe, the blood vessel identification method comprising:
   generating tomographic images of the subject based on the reflected ultrasound waves;
   generating blood flow information of a plurality of frames indicating blood flow regions of the subject in the tomographic images based on the reflected ultrasound waves;
   analyzing the generated flood flow information;
   one of: (i) extracting blood flow points indicating representative points of the blood flow regions to calculate relative positions of the blood flow points across the plurality of frames and extract the blood flow points as a blood flow group, and (ii) comparing areas of the blood flow regions across the plurality of frames to extract the blood flow regions as the blood flow group; and
   determining, for each of a plurality of extracted blood flow groups, whether or not each blood flow region of the blood flow group corresponds to the blood vessel of interest based on at least one of relative positions of the plurality of blood flow groups, area information of the blood flow region, direction information of blood flow, and an attribute of the blood flow group.

20. A non-transitory computer-readable recording medium having a computer program recorded thereon for causing a computer to execute the blood vessel identification method according to claim 19.

21. The blood vessel identification method according to claim 19, wherein whether or not each blood flow region corresponds to the blood vessel of interest is determined by comparing the blood flow information to predetermined data related to said at least one of the relative positions of the plurality of blood flow groups, the area information of the blood flow region, the direction information of blood flow, and the attribute of the blood flow group.

* * * * *